Sept. 5, 1944. A. DICKSON, JR Plant Pat. 639
ROSE PLANT
Filed April 25, 1944
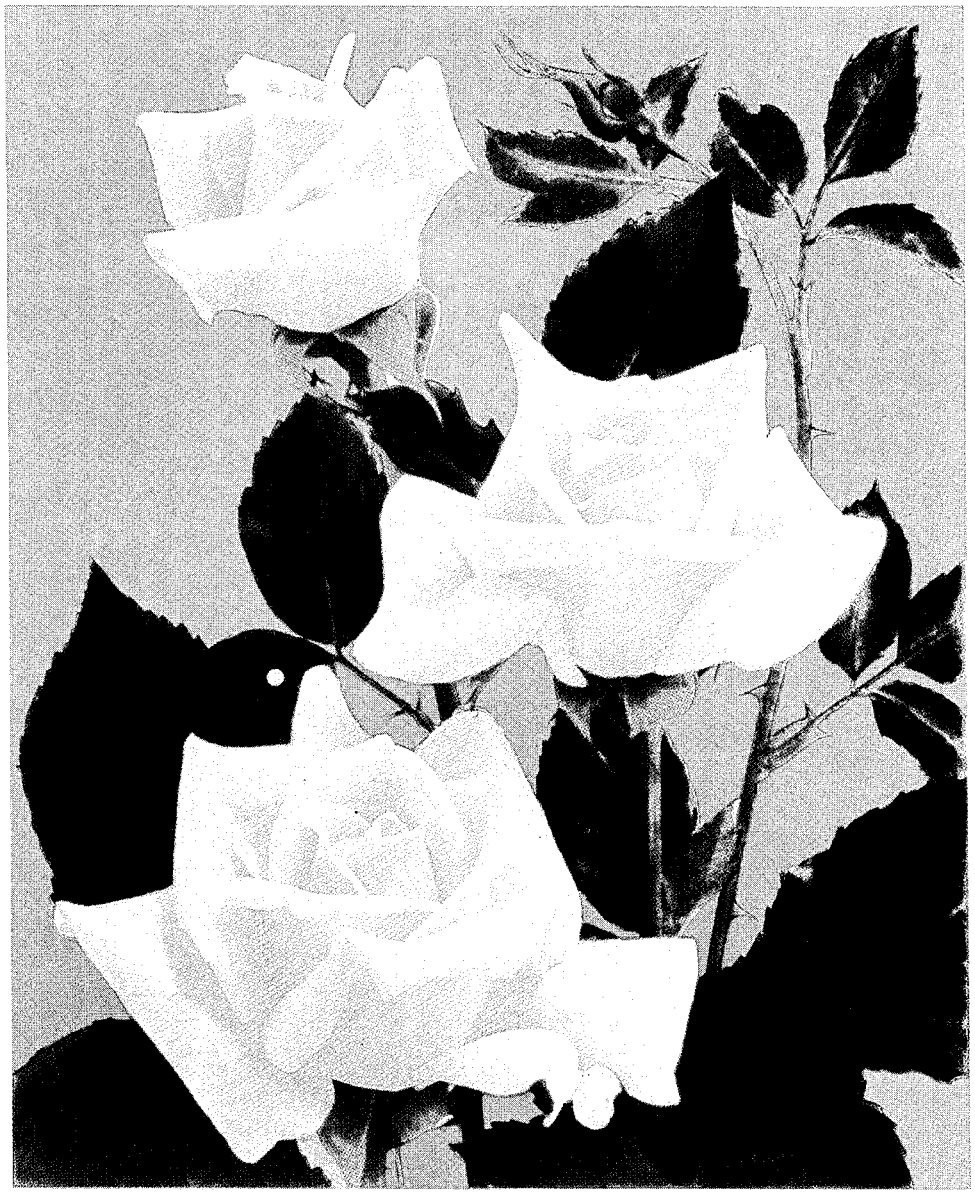
Inventor
Alexander Dickson, Jr.,
By Robb & Robb,
Attorneys Patented Sept. 5, 1944

Plant Pat. 639

UNITED STATES PATENT OFFICE

639

ROSE PLANT

Alexander Dickson, Jr., Newtonards, Belfast, Ireland, assignor to Jackson & Perkins Company, Newark, N. Y., a corporation of New York Application April 25, 1944, Serial No. 532,638

1 Claim. (Cl. 47—61)

The present invention relates to a new and distinct variety of rose plant, originating as a seedling of the cross of the well known "Heinrich Wendland" variety and an unnamed seedling.

Among the dominating characteristics which distinguish this new rose, shown in substantially actual size in the accompanying original illustrations, from prior known varieties, may be mentioned:

(*a*) The color of the bud (Peach Red softened with Rose Doree);

(*b*) The color of the fully opened bloom (Bittersweet Pink lightening to Orient Pink);

(*c*) The Cress Green foliage which makes a perfect background for the pastel-shaded flowers;

(*d*) The high centered flowers which frequently open with a double nose; and (*e*) The prolificacy of bloom throughout the season.

Asexual reproduction of the new variety shows the above characteristics to be established and fixed.

The following is a detailed description of this new variety, color terminology being in accord with Ridgway's Color Standard:

Parentage: Seedling.

*Seed parent.*—"Heinrich Wendland."

*Pollen parent.*—Unnamed seedling.

Classification:

*Botanic and commercial.*—Hybrid tea.

*Flower*

(Observations made in the fields of Jackson & Perkins Company, Newark, New York, in the month of September 1943, in the morning.)

Blooming habit: Recurrent—continuous.

Bud:

*Size.*—Large.

*Form.*—Pointed. Is not affected by wet or hot weather.

*Color.*—When sepals first divide—Rose Doree, Plate 1. When petals begin to unfurl—Peach Red, Plate 1, lightly overcast with Rose Doree, Plate 1. When half blown: inside of petals—Orient Pink, Plate 2, overlaid with Grenadine Pink, Plate 2; reverse of petals—Peach Red, Plate 1, overcast with Grenadine Pink, Plate 2.

*Sepals.*—Serrated; slightly branched. Curl back when petals begin to unfurl. Color—inside—Pale Veronese Green, Plate 18; outside—Lettuce Green, Plate 5.

*Calyx.*—Shape—apple. Size—broad. Aspect—smooth. Color—Lettuce Green, Plate 5. Odor when rubbed—none.

*Peduncle.*—Length—medium. Aspect—rough. Color—Oil Green, Plate 5. Strength—erect; slender.

*Opening.*—Opens up well; is not affected by adverse conditions.

Bloom:

*Size.*—Large; average size when fully expanded, 4½".

*Borne.*—Singly or several together.

*Stems.*—Medium length; strong.

*Form.*—When first open, high center (flowers have double centers when opening). Permanence—retains its form to the end.

*Petalage.*—Double (full but open center). Number of petals under normal conditions, 30 to 35.

*Color.*—Center of flower—Grenadine Pink, Plate 2. Outer petals—Bittersweet Pink, Plate 2. Base of petals (aiglet)—Lemon Chrome, Plate 4. Inside of petals—Bittersweet Pink, Plate 2, lightening to Orient Pink, Plate 2, at edges. Reverse of petals—Grenadine Pink, Plate 2, overcast with Shrimp Pink, Plate 1. General tonality from a distance—between Grenadine Pink, Plate 2, and Bittersweet Pink, Plate 2.

*Discoloration.*—General tonality at end of first day—between Grenadine Pink, Plate 2, and Bittersweet Pink, Plate 2. Second day—between Grenadine Pink, Plate 2, and Bittersweet Pink, Plate 2. Third day—Grenadine Pink, Plate 2; overcast with Orient Pink, Plate 2.

Petals:

*Texture.*—Leathery; is not affected by wet or hot weather.

*Appearance.* — Inside — satiny. Outside—Shiny.

*Form.*—Oval, pointed.

*Arrangement.*—Imbricated (regularly arranged shinglelike). Petaloids in center—few; large.

*Persistence.*—Drop off cleanly.

*Fragrance.*—Moderate. Nature—tea (average hybrid tea scent).

*Lasting quality.*—On the plant and as cut flower—long.

Genital organs:

*Stamens, Anthers.*—Large; many. Color—Lemon Chrome, Plate 4. Arrangement—regular around styles.

*Stamens, filaments.*—Long. Color—Grenadine, Plate 2.
*Pollen.*—Empire Yellow, Plate 4.
*Styles.*—Bunched; uneven length; short; thin.
*Stigmas.*—Pale Orange Yellow, Plate 3.
*Ovaries.*—All enclosed in calyx.

*Plant*

Form: Bush.
Growth: Vigorous; branching.
Foliage: Five leaflets.
*Size.*—Large.
*Quantity.*—Abundant.
*Color.*—New foliage: upper side—Yellowish Oil Green, Plate 5, edges Oxblood Red, Plate 1; under side—Acajou Red, Plate 13. Old foliage: upper side—Cress Green, Plate 31; under side—Rainette Green, Plate 31.
*Shape.*—Oval pointed.
*Texture.*— Upper side — leathery; glossy. Under side—smooth. Ribs and veins—prominent.
*Edge.*—Serrated (saw toothed).
*Serration.*—Single; sharp.
*Leaf stem.*—Absinthe Green, Plate 31. Under side—smooth.
*Stipules.*—Medium length; smooth.
*Disease resistance.*—Resistant insofar as this is evidenced by absence of any disease throughout development and establishment of this variety.
Wood:
*New wood.*—Acajou Red, Plate 13. Bark—smooth.
*Old wood.*—Jade Green, Plate 31. Bark—smooth.
Thorns (thorns are divided into thorns, prickles, and short needles):
*Thorns.*—On main stalks from base and on laterals from stalk—ordinary. Form—broad base; long; hooked downward. Color when young—Acajou Red, Plate 13. Position—irregular.
*Prickles.*—On main stalks and on laterals—none.
*Short needles.*—On main stalks and on laterals—none.

I claim:

A new and distinct variety of rose plant, characterized as to novelty by the novel colorings of the bud and open bloom in combination with the particular green background of the foliage, the high centered form and large size of the flowers, and prolificacy of blooming throughout the season, substantially as shown and described.

ALEXANDER DICKSON, JR.